United States Patent
Wong et al.

(10) Patent No.: US 10,065,904 B2
(45) Date of Patent: Sep. 4, 2018

(54) PROCESS FOR PRODUCING ALKYLATED AROMATIC HYDROCARBONS FROM A MIXED HYDROCARBON FEEDSTREAM

(71) Applicant: SABIC GLOBAL TECHNOLOGIES B.V., Bergen op Zoom (NL)

(72) Inventors: Kae Shin Wong, Geleen (NL); Andrew Mark Ward, Stockton-on-Tees (GB)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/506,429

(22) PCT Filed: Aug. 27, 2015

(86) PCT No.: PCT/EP2015/069611
§ 371 (c)(1),
(2) Date: Feb. 24, 2017

(87) PCT Pub. No.: WO2016/030447
PCT Pub. Date: Mar. 3, 2016

(65) Prior Publication Data
US 2017/0253542 A1  Sep. 7, 2017

(30) Foreign Application Priority Data

Aug. 28, 2014  (EP) ..................................... 14182689

(51) Int. Cl.
C07C 2/66 (2006.01)
C10G 11/05 (2006.01)
C10G 9/00 (2006.01)

(52) U.S. Cl.
CPC ................. *C07C 2/66* (2013.01); *C10G 9/00* (2013.01); *C10G 11/05* (2013.01); C07C 2529/70 (2013.01); C10G 2400/20 (2013.01); C10G 2400/22 (2013.01)

(58) Field of Classification Search
CPC ....... C07C 2529/70; C07C 2/66; C10G 11/05; C10G 2400/20; C10G 2400/22; C10G 9/00
See application file for complete search history.

(56) References Cited

U.S. PATENT DOCUMENTS

| | | | |
|---|---|---|---|
| 3,907,663 A | 9/1975 | Owen | |
| 4,587,370 A | 5/1986 | Degraff | |
| 5,648,579 A | 7/1997 | Kulpranthipanja et al. | |
| 5,902,917 A * | 5/1999 | Collins | C07C 15/073 585/315 |
| 6,177,600 B1 | 1/2001 | Netzer | |
| 6,339,179 B1 | 1/2002 | Schulz et al. | |
| 7,238,843 B2 | 7/2007 | Pohl | |
| 7,795,485 B2 | 9/2010 | Schultz | |
| 8,222,467 B2 | 7/2012 | Brown | |
| 2006/0224031 A1 | 10/2006 | Jan et al. | |
| 2008/0194890 A1 | 8/2008 | Brown | |
| 2008/0194896 A1 | 8/2008 | Brown et al. | |
| 2009/0112029 A1 | 4/2009 | Schultz | |

FOREIGN PATENT DOCUMENTS

| | | |
|---|---|---|
| CN | 103289730 A | 9/2013 |
| KR | 1020130008595 A | 1/2013 |
| WO | 9611175 A1 | 4/1996 |
| WO | 02057204 A1 | 7/2002 |
| WO | 03093230 A2 | 4/2003 |
| WO | 2007068008 A2 | 6/2007 |
| WO | 2010021773 A2 | 2/2010 |
| WO | 2010080190 A1 | 7/2010 |
| WO | 2010092466 A1 | 8/2010 |
| WO | 2011046547 A1 | 4/2011 |
| WO | 2012050655 A2 | 4/2012 |

OTHER PUBLICATIONS

Hwang, et al., "Cumene—Kirk Othmer Encyclopedia of Chemical Technology", 2010, pp. 1-10.
International Search Report for International Application No. PCT/EP2015/069611; dated Nov. 2, 2015; 4 Pages.
Vora et al., "Alkylation—Kirk Othmer Encyclopedia of Chemical Technology", 2003, vol. 2, 35 pages.
Written Opinion of the International Search Report for International Application No. PCT/EP2015/069611; dated Nov. 2, 2015; 7 Pages.
Chinese Publication No. 103289730(A), Date of Publication: Sep. 11, 2013, 6 Pages, Abstract Only.
Korean Publication No. 100881876, Date of Publication: Feb. 6, 2009, Englishe Translation, 121 pages.
Korean Publication No. 1020130008595(A), Date of Publication: Janaury 22, 2013, 1 Page, Abstract Only.

(Continued)

*Primary Examiner* — Sharon Pregler
(74) *Attorney, Agent, or Firm* — Cantor Colburn LLP

(57) ABSTRACT

The invention relates to a process for producing alkylated aromatic hydrocarbons comprising the steps of: (a) subjecting a mixed hydrocarbon feedstream comprising benzene to a separation to provide a C6 cut comprising benzene, wherein the C6 cut comprises at least 60 wt-% of C6 hydrocarbons; (b) subjecting the C6 cut to catalytic cracking or thermal cracking to provide a cracking product stream comprising benzene and C2-C4 alkenes and (c) after step (b), without pre-separation of the cracking product stream, subjecting the cracking product stream to conditions suitable for alkylation to provide an alkylation product stream rich in alkylated aromatic hydrocarbons, wherein the process further comprises the steps of separating benzene and benzene coboilers from the alkylation product stream to obtain a stream of benzene and benzene coboilers and wherein the stream of benzene and benzene coboilers is separated into a benzene-rich stream comprising a higher proportion of benzene than the stream of benzene and benzene coboilers and a benzene-lean stream comprising a lower proportion of benzene than the stream of benzene and benzene coboilers and wherein the benzene-lean stream is recycled back to the catalytic cracking or thermal cracking in step (b).

15 Claims, No Drawings

(56) References Cited

OTHER PUBLICATIONS

Laredo, G. et al. "Benzene reduction in gasoline by olefin alkylationL Effect of the catalyst on a C6-reformate heart-cut" Applied Catalysis A: General, 2009, vol. 363, pp. 19-26.

* cited by examiner

PROCESS FOR PRODUCING ALKYLATED AROMATIC HYDROCARBONS FROM A MIXED HYDROCARBON FEEDSTREAM

CROSS REFERENCE TO RELATED APPLICATIONS

This application is a 371 of International Application No. PCT/EP2015/069611, filed Aug. 27, 2015, which claims priority to European Application No. 14182689.1, filed Aug. 28, 2014, both of which are incorporated herein by reference in their entirety.

The invention is directed to a process for producing alkylated aromatic hydrocarbons such as ethylbenzene or cumene from a mixed hydrocarbon feedstream.

The commercial production of the benzene derivatives ethylbenzene ("EB") or cumene comprises the alkylation of benzene using ethylene or propylene as alkylation agent; see e.g. Hwang and Chen (2010) Cumene Kirk-Othmer Encyclopedia of Chemical Technology 1-10.

One known method for producing high-purity ethylbenzene or cumene is to provide a pure benzene stream and subject it to alkylation. In this method, a mixed hydrocarbon feedstream such as a reformate or a C6 cut is typically subjected to aromatic extraction, such as liquid extraction or extractive distillation, to remove the benzene co-boilers in order to provide a sufficiently purified benzene stream. A drawback of such a process is that aromatic extraction methods are expensive and time consuming.

U.S. Pat. No. 6,177,600 describes a process for the simultaneous coproduction of ethylbenzene and ethylene. In this process, ethylene and a dilute ethylene mixture are produced by conventional steam cracking and downstream propylene separation. Impure benzene mixture is separately produced by hydrogenation and fractionation of pyrolysis gasoline. The dilute ethylene mixture and the impure benzene mixture are fed to an ethylbenzene production zone to be reacted. High purity ethylbenzene is obtained after a series of products fractionation and purifications.

U.S. Pat. No. 8,222,467 describes a process for the propylation of benzene to produce high purity cumene that uses a hydrocarbon composition feed containing benzene that has not undergone extraction. The hydrocarbon composition is formed by steam cracking naphtha. C4− hydrocarbons is removed from the cracked naphtha; subsequently sulfur and nitrogen are removed and the resulting product is distilled to form a C5− fraction and a C6+ fraction. The C6+ fraction is treated to remove olefins and dienes and the resulting product is fractionated to form a C6 fraction and a C7+ fraction. The C6 fraction comprising benzene/benzene coboiler is introduced to a propylation zone. In the propylation zone, propylene is introduced and benzene is reacted with the propylene to form cumene. Cumene is recovered from the cumene-containing product by successive fractionation.

While these processes produce alkylated aromatic hydrocarbons without the expensive and time consuming extraction step, there is a constant need in the industry for a simpler and less energy intensive process.

Accordingly, the invention provides a process for producing alkylated aromatic hydrocarbons comprising the steps of:

(a) subjecting a mixed hydrocarbon feedstream to a separation to provide a C6 cut comprising benzene, wherein the C6 cut comprises at least 60 wt-% of C6 hydrocarbons;

(b) subjecting the C6 cut to catalytic cracking or thermal cracking to provide a cracking product stream comprising benzene and C2-C4 alkenes;

(c) after step (b), without pre-separation of the cracking product stream, subjecting the cracking product stream to conditions suitable for alkylation to provide an alkylation product stream rich in alkylated aromatic hydrocarbons, wherein the process further comprises the steps of separating benzene and benzene coboilers from the alkylation product stream to obtain a stream of benzene and benzene coboilers and wherein the stream of benzene and benzene coboilers is separated into a benzene-rich stream comprising a higher proportion of benzene than the stream of benzene and benzene coboilers and a benzene-lean stream comprising a lower proportion of benzene than the stream of benzene and benzene coboilers and wherein the benzene-lean stream is recycled back to the catalytic cracking or thermal cracking in step (b).

According to the invention, both benzene and alkenes required for the production of the alkylated benzene are provided from a single feed, which is a C6 cut. The C6 cut is subjected to cracking, by which alkenes are produced while most of the benzene in the C6 cut are preserved. The cracking product stream comprising the benzene and the alkenes is subjected to conditions suitable for alkylation without further pre-separation. Accordingly, the present invention advantageously provides a process which does not require separate sources for benzene and alkenes as in the prior art.

The alkylated aromatic hydrocarbons can be separated from the alkylation product stream by simple distillation. Accordingly, high purity alkylated aromatic hydrocarbons can be obtained by a simple process according to the present invention. The alkylation product stream can also be separated from each other, e.g. a high purity cumene can be obtained from the alkylation product stream by distillation.

In step (b), a cracking product stream is obtained comprising benzene and C2-C4 alkenes. The amount of benzene coboilers in the cracking product stream is reduced compared to the C6 cut due to the cracking.

The cracking product stream typically further comprises C1-C4 alkanes produced by the cracking. These C1-C4 alkanes remain in the alkylation product stream obtained by step (c). On the other hand, the alkylation product stream comprises little or no alkene, since alkenes have reacted with excess benzene present in the cracking product stream. Accordingly, the C1-C4 alkanes can advantageously be separated from the alkylation product stream without energy intensive separation between alkanes and alkenes.

In addition to the alkylated aromatic hydrocarbons, the alkylation product stream further comprises unreacted benzene and benzene coboilers, which can be isolated from the alkylation product stream by simple distillation. The unreacted benzene and benzene coboilers can be recycled back to be subjected to cracking in step (b) and/or alkylation in step (c), after further separation between the benzene and benzene coboilers.

US2009/112029 discloses an integrated process for catalytically cracking a heavy hydrocarbon feedstock, obtaining a combined propane/propylene stream, and reacting the propylenes of the combined propane/propylene stream with benzene to produce a cumene product stream.

US2008/194896 discloses a process for producing a high purity ethylbenzene product by providing a hydrocarbon composition feed substantially free of C4− hydrocarbons and C7+ aromatic hydrocarbons, and contains benzene and C6+ non-aromtaich hydrocarbons, alkylating the benzene in the hydrocarbon composition feed with ethylene and distilling the product.

U.S. Pat. No. 5,902,917 discloses a process for producing ethylbenzene or cumene, by introducing a feed comprising benzene and polyalkylbenzene into a translakylation reactor and, introducing the entire effluent and ethylene or propylene into an alkylation reactor. U.S. Pat. No. 5,902,917 further discloses the separation of the effluent from the alkylation zone into alkene, benzene, alkylbenzene and polyalkylbenzenes. The polyalkylbenzenes are recycled back to transalkylation. The benzene from the separator is introduced to the transalkylation reactor and the alkylation reactor.

US2009/112029, US2008/194896 and U.S. Pat. No. 5,902,917 do not disclose separating benzene and benzene coboilers from the alkylation product stream to obtain a stream of benzene and benzene coboilers, separating said stream into a benzene-rich stream and a benzene-lean stream and recycling the benzene-lean stream to the catalytic cracking or thermal cracking. In U.S. Pat. No. 5,902,917, part of the benzene from the separator is introduced to the transalkylation reactor and part of the benzene from the separator is introduced to the alkylation reactor. In U.S. Pat. No. 5,902,917 the benzene from the separator is not separated into a relatively benzene-rich stream and a relatively benzene-poor stream before the recycle. In contrast, according to the present invention, the stream comprising benzene and benzene coboilers is separated such that benzene primarily ends up in one stream (benzene-rich stream) and benzene coboilers primarily end up in another stream (benzene-lean stream). The benzene-lean stream which mainly comprises benzene coboilers is recycled back to the catalytic cracking or thermal cracking according to the invention. Compared to recycling benzene to the transalkylation reactor as in U.S. Pat. No. 5,902,917, providing a benzene-lean stream and then recycling the benzene-lean stream to the catalytic cracking or thermal cracking leads to a more efficient use of benzene and the benzene coboilers.

Definitions

The term "aromatic hydrocarbons" or "aromatics" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

As used herein, the term "C# hydrocarbons", or "C#", wherein "#" is a positive integer, is meant to describe all hydrocarbons having # carbon atoms. Moreover, the term "C#+ hydrocarbons" is meant to describe all hydrocarbon molecules having # or more carbon atoms. Accordingly, the term "C9+ hydrocarbons" is meant to describe a mixture of hydrocarbons having 9 or more carbon atoms. The term "C9+ alkanes" accordingly relates to alkanes having 9 or more carbon atoms. The term "C2-3 alkane" accordingly relates to alkanes having 2 or 3 carbon atoms. The term "C2-3 alkene" accordingly relates to alkenes having 2 or 3 carbon atoms.

In the process of the present invention, any mixed hydrocarbon composition that comprises benzene and that is suitable to be subjected to catalytic cracking or thermal cracking to provide a stream comprising benzene and C2-C4 alkenes can be used as a feedstream.

Examples of suitable feedstream include reformate, straight run naphtha, hydrocracked gasoline, light coker naphtha, coke oven light oil, natural gas condensates, pyrolysis gasoline and FCC gasoline, and mixtures thereof.

Step (a)

The process of the present invention comprises subjecting a mixed hydrocarbon feedstream to a separation to provide a C6 cut. As used herein, the term "C6 cut" relates to a hydrocarbon fraction comprising at least 60 wt-% C6 hydrocarbons, preferably at least 70 wt-% C6 hydrocarbons, more preferably at least 80 wt-% C6 hydrocarbons, particularly preferably at least 90 wt-% C6 hydrocarbons, more particularly preferably at least 95 wt-% C6 hydrocarbons, and most preferably at least 99 wt-% C6 hydrocarbons. Preferably, the separation to provide a C6 cut does not involve aromatic extraction, such as liquid extraction or extractive distillation. Preferably, the separation to provide a C6 cut involves distillation. The skilled person is capable of selecting the suitable distillation conditions to provide a C6 cut as defined herein. Preferably, the distillation conditions are suitable to provide a C6 cut having a boiling point range of 45-95° C., more preferably of 47-90° C., particularly preferably of 48-85° C. and most preferably 49-81° C. The hydrocarbons comprised in the mixed hydrocarbon feedstream and which are not comprised in the C6 cut, such as the C7+ cut, may be subjected to further chemical processing or separation or may be used as such. Preferably, the C7+ cut is added to the gasoline blending pool.

Step (b)

In step (b), a cracking product stream is obtained comprising benzene and C2-C4 alkenes. The cracking product stream typically further comprises C1-C4 alkanes produced by the cracking. The cracking product stream typically further comprises benzene coboilers, but the amount of the benzene coboilers is reduced compared to the C6 cut due to the cracking.

Catalytic Cracking

The catalytic cracking involves the presence of acid catalysts (usually solid acids such as silica-alumina and zeolites) which promote a heterolytic (asymmetric) breakage of bonds yielding pairs of ions of opposite charges, usually a carbocation and the very unstable hydride anion. Carbon-localized free radicals and cations are both highly unstable and undergo processes of chain rearrangement, C-C scission in position beta as in cracking, and intra- and intermolecular hydrogen transfer. In both types of processes, the corresponding reactive intermediates (radicals, ions) are permanently regenerated, and thus they proceed by a self-propagating chain mechanism. The chain of reactions is eventually terminated by radical or ion recombination.

According to the process of the invention, the catalytic cracking may be performed in a gas phase fixed bed reactor or a fluidized bed reactor. Both a gas phase fixed bed reactor and a fluidized bed reactor are well-known in the art.

In a fluid bed reactor for catalytic cracking (=fluid catalytic cracker, FCC), cracking takes place generally using a very active zeolite-based catalyst in a short-contact time vertical or upward-sloped pipe called the "riser". Pre-heated feed is sprayed into the base of the riser via feed nozzles where it contacts extremely hot fluidized catalyst. Preferred process conditions used for fluid catalytic cracking generally include a temperature of 425-700° C. and a pressure of 10-800 kPa gauge. The hot catalyst vaporizes the feed and catalyzes the cracking reactions that break down the high-molecular weight hydrocarbons into lighter components including LPG, light-distillate and middle-distillate. The catalyst/hydrocarbon mixture flows upward through the riser for a few seconds, and then the mixture is separated via cyclones. The catalyst-free hydrocarbons are obtained to be further processed. "Spent" catalyst is disengaged from the cracked hydrocarbon vapors and sent to a stripper where it is contacted with steam to remove hydrocarbons remaining in the catalyst pores. The "spent" catalyst then flows into a fluidized-bed regenerator where air (or in some cases air plus oxygen) is used to burn off the coke to restore catalyst activity and also provide the necessary heat for the next reaction cycle, cracking being an endothermic reaction. The "regenerated" catalyst then flows to the base of the riser, repeating the cycle. The process of the present invention may comprise several FCC units operated at different process conditions, depending on the hydrocarbon feed and the desired product slate.

In some preferred embodiments, the catalytic cracking is performed in a gas phase fixed bed reactor. This allows easier operation and control. The use of the fixed bed reactor is made possible by the fact that the cracking feed consists of a C6 cut, which makes the deactivation of the catalyst much slower than a cracking feed of a mixed hydrocarbons. The catalyst and the process conditions suitably used for the catalytic cracking in a fixed bed reactor may be the same as the ones described herein for the catalytic cracking in a fluidized bed reactor.

Thermal Cracking

Step (b) may involve thermal cracking, which is also called steam cracking.

In steam cracking the hydrocarbon feeds are diluted with steam and briefly heated in a furnace without the presence of oxygen. Typically, the reaction temperature is 750-900° C. and the reaction is only allowed to take place very briefly, usually with residence times of 50-1000 milliseconds. Preferably, a relatively low process pressure is to be selected of atmospheric up to 175 kPa gauge.

After the cracking temperature has been reached, the gas is quickly quenched to stop the reaction in a transfer line heat exchanger or inside a quenching header using quench oil. Steam cracking results in the slow deposition of coke, a form of carbon, on the reactor walls. Decoking requires the furnace to be isolated from the process and then a flow of steam or a steam/air mixture is passed through the furnace coils. This converts the hard solid carbon layer to carbon monoxide and carbon dioxide. Once this reaction is complete, the furnace is returned to service. The products produced by steam cracking depend on the composition of the feed, the hydrocarbon to steam ratio and on the cracking temperature and furnace residence time.

Catalytic cracking results in a higher propylene/ethylene ratio than thermal cracking. Accordingly, catalytic cracking is preferred for producing more cumene in the final product and thermal cracking is preferred for producing ethylbenzene in the final product.

Preferably, the conditions of step (b) are selected such that the molar ratio of the benzene to the C2-C4 alkenes in the cracking product stream is 3-10, for example 5-8.

Step (c)

The cracking product stream is directly subjected to conditions suitable for alkylation without further separation. In some embodiments, the cracking product stream is quenched before being subjected to alkylation. The benzene and the C2-C4 alkenes in the cracking product stream react to form alkylated benzenes in step (c). Excess benzene is present in the cracking product stream with respect to the alkenes, so substantially all alkenes reacted with benzene. Hence, the alkylation product stream comprises substantially no alkene.

In this step, the cracking product stream is contacted with an alkylation catalyst under alkylation conditions. The process conditions suitable for alkylation, also described herein as "alkylation conditions", can be easily determined by the person skilled in the art; see e.g. Vora et al. (2003) Alkylation Kirk-Othmer Encyclopedia of Chemical Technology and Hwang and Chen (2010) loc. cit. The process conditions used for alkylation generally includes a process temperature of 100-300° C., a pressure of 0.5-10 MPa, a weight hourly space velocity of 0.5-20 $h^{-1}$ and benzene/C2-C4 alkenes molar ratio of 3-10. The benzene alkylation process step uses an acidic catalyst which may be a solid phosphoric acid catalyst (phosphoric acid supported on alumina) or an aluminum chloride complex as the catalyst or an acidic zeolite-based catalyst. Preferably, the zeolite comprised in the alkylation catalyst has a pore size of 6-8 Å. The optimal process conditions depend on the proportions of C2-C4 alkenes in the stream to be subjected to alkylation. For instance, when more cumene is desired in the alkylation product stream the process conditions are somewhat milder compared to when more ethybenzene is desired in the alkylation product stream.

The molar ratio of the benzene to the C2-C4 alkenes in the stream to be subjected to alkylation is preferably 3-10, for example 5-8. This can be achieved by selecting the conditions of step (b) such that the molar ratio of the benzene to the C2-C4 alkenes in the cracking product stream is 3-10, for example 5-8. The molar ratio of the benzene to the C2-C4 alkenes in the stream to be subjected to alkylation can also be adjusted by recycling back the benzene from the alkylation product stream. The molar ratio of the benzene to the C2-C4 alkenes in the stream to be subjected to alkylation is influenced by the molar ratio of the benzene to C6 aliphatics in the C6 cut. The recycling back of the benzene is especially advantageous when the molar ratio of the benzene to C6 aliphatics in the C6 cut is low.

The alkylation catalyst preferably comprises beta zeolite, zeolite Y, ZSM-12, MCM-22 and mordenite.

The alkylation conditions preferably comprise a temperature of 120-250° C. preferably of 150-230° C. a pressure of 1000-5000 kPa, preferably of 2500-3500 kPa, a Weight Hourly Space Velocity (WHSV) of 0.5-20 $h^{-1}$, preferably of 1-10 $h^{-1}$ and a benzene/C2-C4 alkenes molar ratio of 3-10, for example 5-8.

Step (d)

Typically, the alkylation product stream comprises hydrogen; C1-C4 alkanes; benzene and benzene coboilers; and alkylated aromatic hydrocarbons.

Preferably, the process of the invention further comprises the step of (d) separating the alkylated aromatic hydrocarbons from the alkylation product stream, preferably by distillation. Preferably, the process further comprises the step of separating ethylbenzene from the alkylated aromatic hydrocarbons and/or the step of separating cumene from the alkylated aromatic hydrocarbons. In particular, cumene can be separated from the alkylated aromatic hydrocarbons aromatic hydrocarbon stream by simple distillation since the alkylated aromatic hydrocarbons aromatic hydrocarbon stream comprises substantially no coboilers of cumene.

Preferably, step (d) comprises separating the alkylated aromatic hydrocarbons into a C7-C9 aromatic hydrocarbon stream and a C10+ aromatic hydrocarbon stream, preferably by distillation.

The C7-C9 alkylated aromatic hydrocarbon stream comprises toluene, ethylbenzene and cumene and other alkylated aromatic hydrocarbons. Different types of the C7-C9 alkylated aromatic hydrocarbons can be separated from each other by distillation and/or other known separation methods. Preferably, step (d) further comprises separating the C7-C9 alkylated aromatic hydrocarbon stream into toluene, ethylbenzene, cumene and remaining components.

The C10+ alkylated aromatic hydrocarbon stream comprises monoalkylated aromatic hydrocarbons with a C4+ alkyl group (e.g. butylbenzene) and polyalkylated aromatic hydrocarbons. The term "monoalkylated aromatic hydrocarbon" is herein understood to mean an aromatic hydrocarbon having one alkyl group. The term "polyalkylated aromatic hydrocarbon" is herein understood to mean an aromatic hydrocarbon having more than one alkyl groups. The polyalkylated aromatic hydrocarbons include e.g. diethylbenzene, triethylbenzene, diisopropyibenzene and triisopropyibenzene. Preferably, the C10+ alkylated aromatic hydrocarbon stream is recycled back to the catalytic cracking or thermal cracking in step (b). One or more of the alkyl groups of the recycled C10+ alkylated aromatic hydrocarbons are removed by the cracking step (b), which results in monoalkylated aromatic hydrocarbons such as ethylbenzene and cumene or benzene. More amount of ethylbenzene and cumene is hence obtained according to this embodiment by cracking of the recycled C10+ alkylated aromatic hydrocarbons. Further the amount of produced benzene may be increased by cracking of the recycled C10+ alkylated aromatic hydrocarbons according to this embodiment of the invention.

The alkylation product stream comprises unreacted benzene and benzene coboilers. The process further comprises the step of separating benzene and benzene coboilers from the alkylation product stream to obtain a stream of benzene and benzene coboilers, preferably by distillation.

At least part of the stream of benzene and benzene coboilers can be recycled back to the catalytic cracking or thermal cracking in step (b). Additionally or alternatively, at least part of the stream of benzene and benzene coboilers may be recycled back to the alkylation in step (c). The recycling of the benzene and benzene coboilers to cracking in step (b) and/or alkylation in step (c) increases the amount of alkylated hydrocarbons produced according to the present invention.

Before the recycling, the stream of benzene and benzene coboilers is further separated into a benzene-rich stream comprising a higher proportion of benzene than the stream of benzene and benzene coboilers and a benzene-lean stream comprising a lower proportion of benzene than the stream of benzene and benzene coboilers. This separation may be carried out by any applicable means including but not limited to distillation, extractive distillation or solvent extraction. The benzene-rich stream is preferably recycled back for the alkylation in step (c). The benzene-lean stream is recycled back for the catalytic cracking or thermal cracking in step (b).

The benzene-rich stream comprises a higher proportion of benzene than the stream to be separated, i.e. the stream of benzene and benzene coboilers separated from the alkylation product stream. Similarly, the benzene-lean stream comprises a lower proportion of benzene than the stream of benzene and benzene coboilers. Due to this adjustment of the benzene proportion prior to the recycling, a more efficient use of benzene and benzene coboilers is achieved compared to a recycling without the adjustment of the benzene proportion.

The separation is performed such that a higher amount of benzene in the stream of benzene and benzene coboilers ends up in the benzene-rich stream, i.e. the separation results in more than 50 wt %, preferably more than 60 wt %, more preferably more than 70 wt %, more preferably more than 80 wt %, more preferably more than 90 wt %, more preferably more than 95 wt %, more preferably more than 98 wt %, more preferably more than 99 wt %, more preferably more than 99.5 wt % of the benzene in the stream of benzene and benzene coboilers being present in the benzene-rich stream after the separation. In most preferred case, all benzene in the stream of benzene and benzene coboilers end up in the benzene-rich stream.

Preferably, the difference in the proportion of benzene in the benzene-rich stream and the proportion of benzene in the benzene-lean stream is at least 5 wt %, more preferably at least 10 wt %, more preferably at least 20 wt %, more preferably at least 30 wt %, more preferably at least 50 wt %. Preferably, the amount of benzene in the benzene-rich stream is at least 80 wt %, more preferably at least 90 wt %, more preferably at least 95 wt %, more preferably at least 98 wt %, more preferably at least 99 wt %, most preferably 100 wt %. Preferably, the amount of benzene in the benzene-lean stream is less than 20 wt %, more preferably less than 10 wt %, more preferably less than 5 wt %, more preferably less than 3 wt %, more preferably less than 1 wt %, most preferably 0 wt %.

Since the alkylation product stream does not contain C2-C4 alkenes, the C1-C4 alkanes can advantageously be separated from the alkylation product stream without energy intensive separation between alkanes and alkenes. Accordingly, preferably, the process further comprises the step of separating C1-C4 alkanes from the alkylation product stream, preferably by distillation.

In preferred embodiments, step (d) comprises
(d1) separating the alkylation product stream into a gas stream comprising hydrogen and C1-C4 alkanes and a liquid stream comprising benzene and benzene coboilers and alkylated aromatic hydrocarbons, preferably by distillation.

Preferably, step (d) further comprises
(d2) separating the liquid stream obtained by step (d1) into a stream comprising benzene and benzene coboilers and a stream comprising the alkylated aromatic hydrocarbons, preferably by distillation.

Preferably, step (d) further comprises
(d3) separating the stream comprising the alkylated aromatic hydrocarbons obtained by step (d2) into a C7-C9 alkylated aromatic hydrocarbon stream and a C10+ alkylated aromatic hydrocarbon stream, preferably by distillation.

Preferably, step (d) further comprises
(d4) separating the C7-C9 alkylated aromatic hydrocarbon stream obtained by step (d4) into toluene, ethylbenzene, cumene and remaining components.

Preferably, the gas stream obtained by step (d1) is subjected to distillation to separate hydrogen, methane and C2-C4 alkanes from each other.

System

The process according to the invention may be performed in a single reactor or two or more reactors in series.

In some embodiments, the process is performed in a system comprising a first reactor and a second reactor provided after the first reactor, wherein the first reactor is arranged for performing step (b) and the second reactor is arranged for performing step (c).

No separation unit for the product from the first reactor is present between the first reactor and the second reactor. In some embodiments, a compressor is provided between the first reactor and the second reactor. This provides a higher pressure necessary for alkylation than cracking. In some embodiments, a cooling unit is present between the first reactor and the second reactor.

Step (b) requires a generally higher temperature than step (c). In case of catalytic cracking, the catalytic cracking causes an adiabatic temperature drop. In some cases, the temperature drop is sufficient for achieving the temperature of the cracking product stream suitable for step (c). Accordingly, the process of the invention may be performed in a single reactor comprising a first zone and a second zone provided after the first zone, wherein the first zone is arranged for performing step (b) and the second zone is arranged for performing step (c). This is highly advantageous for reducing CAPEX. In suitable examples, the C6 cut enters the first zone at a temperature of 550-700° C. and the cracking product stream has a temperature of 300° C. The cracking product stream is alkylated at a temperature of 300° C. in the second zone.

The process of the invention may also be performed in a system comprising a first reactor and a second reactor provided after the first reactor, wherein the second reactor comprises a first zone and a second zone provided after the first zone, wherein the first reactor and the first zone of the second reactor are arranged for performing step (b) and the second zone of the second reactor is arranged for performing step (c). In these embodiments, part of the cracking is performed in the first reactor and part of the cracking is performed in the first zone of the second reactor. The cracking in the first reactor is performed at a higher temperature than the cracking in the first zone of the second reactor. A compressor and/or a cooling unit may be present between the first reactor and the second reactor.

It is noted that the invention relates to all possible combinations of features described herein, particularly features recited in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be more fully described by the following non-limiting Examples.

EXAMPLES

Example 1

The composition of a synthetic mixed C6 hydrocarbon stream representing a reformate C6 cut is shown in Table 1. This stream was subjected to catalytic cracking at a temperature of 680° C., a pressure of 1 bar, a steam or water/oil ratio of 2 and WHSV of 1.2 h$^{-1}$.

The catalyst used for the catalytic cracking was a fixed bed catalyst prepared by extruding method. Lanthanum modified ZSM-5 zeolites were active components of the catalyst, Kaolin was used as the structure and activity additives, and alumina gel was used as binder. The extruded catalysts were dried at 110° C. for 12 hours, then calcined at 650° C. for 6 hours and treated by steam at 800° C. for 6 hours. The obtained catalysts were cylinder-shaped granules with 1.6 mm in diameter. The catalysts were crushed into particles with about 20-40 mesh before use and 10 mL of the catalyst was used.

The stream obtained by the catalyst cracking was sent to an alkylation unit (200° C., 25 bar). The catalyst used for the alkylation was zeolite beta.

The resulting compositions of the catalytic cracking and the subsequent alkylation are shown in Table 1. The compositions are in wt %.

As a comparison, the same C6 cut feed was sent to an alkylation unit with the same conditions and catalyst (200° C., 25 bar, zeolite beta), to which propylene was added at a molar ratio of benzene to propylene of 4. The resulting composition is shown in Table 1.

The product distribution is obtained by combination of laboratory experimentation and flowsheet modeling.

TABLE 1

| Components | C6 cut | catalytic cracking followed by alkylation | | direct alkylation |
|---|---|---|---|---|
| | | cracking product stream | alkylation product stream | alkylation product stream |
| Hydrogen | 0 | 0.3 | 0.3 | 0 |
| Methane | 0 | 3.2 | 3.2 | 0 |
| Ethylene | 0 | 9.9 | 0 | 0 |
| Ethane | 0 | 1.8 | 1.8 | 0 |
| Propylene | 0 | 13.2 | 0 | 0 |
| Propane | 0 | 3.5 | 3.5 | 0 |
| Butene | 0 | 4.1 | 0 | 0 |
| Butane | 0 | 6.6 | 6.6 | 0 |
| Benzene | 50 | 50 | 1.7 | 5.1 |
| n-hexane | 15 | 0.8 | 0.8 | 11.8 |
| Cyclohexane | 5 | 0.8 | 0.8 | 3.9 |
| i-hexane | 30 | 1.8 | 1.8 | 23.6 |
| Toluene | 0 | 2.7 | 2.7 | 0 |
| Xylene | 0 | 1.3 | 1.3 | 0 |
| Ethylbenzene | 0 | 0 | 26.2 | 0 |
| Diethylbenzene | 0 | 0 | 5 | 0 |
| Triethylbenzene | 0 | 0 | 1 | 0 |
| Cumene | 0 | 0 | 27.8 | 45.5 |
| Buthylbenzene | 0 | 0 | 9.5 | 0 |
| Diisopropylbenzene | 0 | 0 | 5.4 | 8.9 |
| Triisopropylbenzene | 0 | 0 | 0.6 | 1.2 |
| Total | 100 | 100 | 100 | 100 |

The catalyst cracking product stream mainly consisting of C1-C4 alkanes, C2-C4 alkenes, benzene and benzene coboilers were obtained. The molar ratio of benzene to C2-C4 alkenes is 4.

For direct alkylation of the C6 cut with propylene, large amount of unconverted C6 aliphatics (~40 wt. %) remain in the effluent. On the other hand, with the catalytic cracking followed by the alkylation, large amount of C6 aliphatics have been converted via catalytic cracking and only about 3 wt. % of C6 aliphatics are observed in the subsequent alkylation effluent. Additionally, both benzene and olefin feeds are needed for direct alkylation while only one feed is need for catalytic cracking followed by alkylation as olefin will be produced in situ.

Benzene and benzene coboilers (n-hexane, cyclohexane, i-hexane) are separated from the alkylation product stream. The separated stream comprises benzene and the benzene coboilers at a weight ratio of 1.7:3.4, i.e. about 33 wt % of the stream is benzene. This can easily be performed e.g. by distillation. Subsequently, a separation is performed intended for the separation between benzene and the benzene coboilers. This results in a benzene-rich stream having a benzene proportion of more than 33 wt % and a benzene-lean stream having a benzene proportion of less than 33 wt %. The benzene-lean stream is recycled back to the catalytic cracking to produce alkenes useful for the subsequent alkylation.

Example 2

The C6 cut used in Example 1 was subjected to thermal cracking under various conditions as shown in Table 2. The obtained compositions are also shown in Table 2. The results were obtained by combination of laboratory experimentation and flowsheet modeling.

TABLE 2

|  | cracking product stream | | |
|---|---|---|---|
|  | case1 | case2 | case3 |
| Reaction temperature [° C.] | 800 | 820 | 840 |
| Reaction pressure [bar] | 1.7 | 1.7 | 1.7 |
| Steam or water/Oil | 0.35 | 0.35 | 0.35 |
| Flowrate [tons/hr] | 30 | 30 | 30 |
| Hydrogen (100 wt %) | 0.59 | 0.65 | 0.72 |
| CO | 0.04 | 0.06 | 0.08 |
| CO2 | 0 | 0.01 | 0.01 |
| Methane | 7.58 | 8.52 | 9.37 |
| Acetylene | 0.1 | 0.15 | 0.22 |
| Ethylene | 13.11 | 14.38 | 15.39 |
| Ethane | 1.93 | 1.92 | 1.84 |
| Propadiene | 0.28 | 0.36 | 0.44 |
| Propylene | 8.72 | 8.11 | 7.16 |
| Propane | 0.26 | 0.24 | 0.2 |
| Butadiene | 2.08 | 2.03 | 1.88 |
| Butene | 3.65 | 2.91 | 2.16 |
| Butane | 0.05 | 0.04 | 0.03 |
| Pentane | 0 | 0 | 0 |
| Pentene | 0.82 | 0.43 | 0.21 |
| Pentadiene | 1.14 | 1.03 | 0.82 |
| Benzene | 41.05 | 39.6 | 38.14 |
| n-hexane | 1.12 | 0.5 | 0.18 |
| Cyclohexane | 0.56 | 0.35 | 0.2 |
| i-hexane | 1.67 | 0.75 | 0.27 |
| Toluene | 3.58 | 3.83 | 3.96 |
| Xylenes | 0.25 | 0.28 | 0.31 |
| C7 non-aromatics | 0.15 | 0.09 | 0.04 |
| Ethylbenzene | 0.12 | 0.14 | 0.14 |
| Styrene | 2 | 2.66 | 3.38 |
| C8 non-aromatics | 0.01 | 0.01 | 0 |
| C9+ | 9.11 | 10.94 | 12.84 |
| Total | 99.99 | 99.99 | 99.98 |

Similar to catalytic cracking, mixtures comprising benzene, benzene coboilers and alkenes were obtained. The amount of benzene coboilers was substantially reduced. More ethylene was obtained by thermal cracking and more propylene was obtained by catalytic cracking.

When these cracking product streams are subjected to alkylation condition, alkylated aromatic hydrocarbons are obtained.

The invention claimed is:

1. A process for producing alkylated aromatic hydrocarbons comprising:
    (a) subjecting a mixed hydrocarbon feedstream comprising benzene to a separation to provide a C6 cut comprising benzene, wherein the C6 cut comprises at least 60 wt-% of C6 hydrocarbons;
    (b) subjecting the C6 cut to catalytic cracking or thermal cracking to provide a cracking product stream comprising benzene and C2-C4 alkenes and
    (c) after step (b), without pre-separation of the cracking product stream, subjecting the cracking product stream to conditions suitable for alkylation to provide an alkylation product stream rich in alkylated aromatic hydrocarbons,
    wherein the process further comprises the steps of separating benzene and benzene coboilers from the alkylation product stream to obtain a stream of benzene and benzene coboilers and
    wherein the stream of benzene and benzene coboilers is separated into a benzene-rich stream comprising a higher proportion of benzene than the stream of benzene and benzene coboilers and a benzene-lean stream comprising a lower proportion of benzene than the stream of benzene and benzene coboilers and wherein the benzene-lean stream is recycled back to the catalytic cracking or thermal cracking in step (b).

2. The process according to claim 1, wherein the difference in the proportion of benzene in the benzene-rich stream and the proportion of benzene in the benzene-lean stream is at least 5 wt %.

3. The process according to claim 1, wherein the process further comprises the step of (d) separating the alkylated aromatic hydrocarbons from the alkylation product stream by distillation.

4. The process according to claim 3, wherein step (d) comprises separating the alkylated aromatic hydrocarbons into a C7-C9 alkylated aromatic hydrocarbon stream and a C10+ alkylated aromatic hydrocarbon stream by distillation and the process further comprises the step of recycling back the C10+ alkylated aromatic product stream to the catalytic cracking or thermal cracking in step (b).

5. The process according to claim 1, wherein the benzene-rich stream is recycled back to the alkylation in step (c).

6. The process according to claim 1, wherein the process further comprises the step of separating C1-C4 alkanes from the alkylation product stream.

7. The process according to claim 3, wherein step (d) comprises (d1) separating the alkylation product stream into a gas stream comprising hydrogen and C1-C4 alkanes and a liquid stream comprising benzene and benzene coboilers and alkylated aromatic hydrocarbons;
    (d2) separating the liquid stream obtained by step (d1) into a stream comprising benzene and benzene coboilers and a stream comprising the alkylated aromatic hydrocarbons;
    (d3) separating the stream comprising the alkylated aromatic hydrocarbons obtained by step (d2) into a C7-C9 alkylated aromatic hydrocarbon stream and a C10+ alkylated aromatic hydrocarbon stream and
    (d4) separating the C7-C9 alkylated aromatic hydrocarbon stream obtained by step (d3) into toluene, ethylbenzene, cumene and remaining components.

8. The process according to claim 1, wherein the cracking product stream obtained by step (b) is quenched before step (c).

9. The process according to claim 1, wherein step (b) involves catalytic cracking.

10. The process according to claim 9, wherein step (b) is performed in a gas phase fixed bed reactor.

11. The process according to claim 1, wherein step (b) involves thermal cracking.

12. The process according to claim 1, wherein the process is performed in a system comprising a first reactor and a second reactor provided after the first reactor, wherein the first reactor is arranged for performing step (b) and the second reactor is arranged for performing step (c).

13. The process according to claim 12, wherein a compressor is provided between the first reactor and the second reactor.

14. The process according to claim 1, wherein the process is performed in a system comprising a single reactor comprising a first zone and a second zone provided after the first zone, wherein the first zone is arranged for performing step (b) and the second zone is arranged for performing step (c).

15. The process according to claim 1, wherein the process is performed in a system comprising a first reactor and a second reactor provided after the first reactor, wherein the second reactor comprises a first zone and a second zone provided after the first zone, wherein the first reactor and the first zone of the second reactor are arranged for performing step (b) and the second zone of the second reactor is arranged for performing step (c).

* * * * *